(12) United States Patent
Cottier

(10) Patent No.: US 8,325,347 B2
(45) Date of Patent: Dec. 4, 2012

(54) INTEGRATED OPTICAL SENSOR

(75) Inventor: Kaspar Cottier, Wadenswil (CH)

(73) Assignee: Creoptix GmbH, Wadenswil (CH)

( * ) Notice: Subject to any disclaimer, the term of this patent is extended or adjusted under 35 U.S.C. 154(b) by 458 days.

(21) Appl. No.: 12/530,863

(22) PCT Filed: Mar. 10, 2008

(86) PCT No.: PCT/CH2008/000098
§ 371 (c)(1), (2), (4) Date: Sep. 11, 2009

(87) PCT Pub. No.: WO2008/110026
PCT Pub. Date: Sep. 18, 2008

(65) Prior Publication Data
US 2010/0103429 A1    Apr. 29, 2010

(30) Foreign Application Priority Data

Mar. 13, 2007   (CH) ........................ 0408/07

(51) Int. Cl.
*G01B 9/02* (2006.01)
(52) U.S. Cl. ....................................... 356/477
(58) Field of Classification Search ................... 356/477
See application file for complete search history.

(56) References Cited

U.S. PATENT DOCUMENTS

| | | |
|---|---|---|
| 6,335,793 B1 | 1/2002 | Freeman et al. |
| 6,545,759 B1 * | 4/2003 | Hartman ........................ 356/477 |
| 2005/0135723 A1 * | 6/2005 | Carr et al. ........................ 385/12 |
| 2009/0109441 A1 * | 4/2009 | Hartman ........................ 356/477 |

FOREIGN PATENT DOCUMENTS

| | | |
|---|---|---|
| DE | 4419586 | 12/1995 |
| EP | 1031828 | 8/2000 |
| WO | 93/04357 | 3/1993 |
| WO | 98/22807 | 5/1998 |
| WO | 01/40744 | 6/2001 |
| WO | 2006/071992 | 7/2006 |

OTHER PUBLICATIONS

Clerc, D. et al; "Integrated optical output grating coupler as refractometer and (bio-)chemical sensor"; Sensors and Actuators B; Elsevier Sequoia S.A., Lausanne, Switzerland; vol. 11, No. 1-3; Mar. 1, 1991; pp. 461-465; XP022270763.

Kunz, R.E. et al.; "Optimizing integrated optical chips for label-free (bio-)chemcial sensing"; Analytical and Bioanalytical Chemistry; Springer-Verlag, Belgium; vol. 384, No. 1; Jan. 1, 2006; pp. 180-190; XP019327758.

(Continued)

*Primary Examiner* — Tarifur Chowdhury
*Assistant Examiner* — Jonathon Cook
(74) *Attorney, Agent, or Firm* — Rankin, Hill & Clark LLP

(57) ABSTRACT

An integrated optical sensor for, for example, a (bio)chemical sensor has an optical waveguide (2) having at least two coupling regions (3, 5), which are separated by at least one measurement region (4). A first wave is excited in the waveguide (2) by the first coupling region (3) and passes through the measurement region (4) and the second coupling region (5). A second wave is excited in the second coupling region (5) and subsequently interferes with the first wave. Here, the reduction in amplitude of the first wave by the second coupling region (5) is less than 95%.

15 Claims, 11 Drawing Sheets

OTHER PUBLICATIONS

Wiki, M. et al.; "Novel integrated optical sensor based on a grating coupler triplet"; Biosensors & Bioelectronics; Elsevier Science Publishers; Barking, Great Britain; vol. 13, No. 11; Jan. 1, 1998; pp. 1181-1185; XP002274546.

Wiki, M. et al; "Wavelength-interrogated optical sensor for biochemical applications"; Optics Letters, OSA, Optical Society of America; Washington, D.C.; vol. 25, No. 7; Apr. 1, 2000; pp. 463-465; XP000950352.

* cited by examiner

INTEGRATED OPTICAL SENSOR

The invention is related to the field of label-free optical sensors with high sensitivity, large measuring range, high readout speed and high robustness with respect to manufacturing tolerances, particularly consisting of integrated-optical waveguides and a readout device, and their application to (bio-) chemical sensor units, as they find use, for example, in pharmacology or in diagnostics.

DESCRIPTION OF RELATED ART

Label-free (bio-) chemical sensors based on optical readout schemes are generally known. Compared to widespread marker-based methods using for example fluorescent, absorbing or radioactive markers, these measurement methods have the advantage that the measuring process is not influenced by the presence of a marker. This is important for example for the observation of small molecule binding. Another advantage lies in the potential reduction of costs and time necessary for a measurement, since the marker preparation step is left out before the actual measurement. The main applications of such (bio-) chemical sensors are in the field of drug development, e.g., in the rough selection of potential agents, or the specific characterization of interactions between agents and target molecule. Other important applications lie in the field of diagnostics, for example, in blood or urine tests, the search for pathogens, or in the analysis of allergies. Other applications are, for example, in fields such as process control, food, or environmental.

Amongst others, the requirements for a detection method without marker are: high sensitivity, so that also tiny amounts of substances, the smallest interactions, or the smallest molecules can be observed; a high readout speed, so that a fast (bio-) chemical binding or reaction can be traced with the necessary resolution; the possibility of a massively parallel readout of many measurement areas or subunits of a sensor platform, the latter mainly in the format of micro titer plates which are used in the pharmaceutical industry for high throughput screening (HTS), permitting a parallel readout of up to several hundred or even thousand processes; low cost per measurement point; and a large measurement range, so that different processes with different signal strengths can be observed at the same time.

WO 93/04357 describes a measurement system based on the so-called Surface Plasmon Resonance (SPR) where electromagnetic waves are excited at the surface of metal films by prisms or gratings. This is the most widespread measurement method for label-free sensing of (bio-) chemical processes. A disadvantage of SPR sensors—especially of those based on prism couplers—is the difficulty to offer sensor platforms in a micro titer plate format. Furthermore, the measuring method is inherently sensitive to manufacturing tolerances since it is based on a resonance depending on the (angular) position of the sensor platform, therefore small tolerances must be used and complex calibrations must be carried out, which increases the costs as well as the required measuring time. Another disadvantage consists in the fact that the primary sensitivity of the sensor (the dependence of the measured physical value like angle or wavelength on the parameter to be measured such as adsorption of the molecules) mainly depends on the material of the waveguide and can hardly be influenced by design measures.

EP 1031828 describes a sensor, in which an array of gratings allows the in- and outcoupling of light in a waveguide. The measurement method is suitable for massive-parallel readout. As is the case for SPR sensors, the measuring method is based on an optical resonance, and has the disadvantage of the sensitivity to manufacturing tolerances. Besides, the measurement range is limited by the scanning range of the measured variables such as angle or wavelength, and fast readout speeds could only be shown within a limited measuring range.

WO06/071992 describes a measuring unit which is based on a waveguide-grating. The measuring method is suitable for massive-parallel readout. A disadvantage of this method—even more than in the previous examples and as is described in the patent—is the calibration step required before starting a measurement and the costs associated to it.

U.S. Pat. No. 6,335,793 describes a sensor based on an integrated-optical interferometer. Although the described measurement method shows a large measurement range, it can not or only hardly be integrated into a platform having several measuring points, because the readout of the interferometric signal occurs in a plane situated perpendicular to the waveguide. Furthermore, the manufacture of the sensor platforms as well as the instrument is very cost-intensive, and the extraction of a useful signal from the interference patterns is complex.

BRIEF SUMMARY OF THE INVENTION

It is therefore the objective of the invention to create a sensor unit which can be used in particular for (bio-) chemical measurements of the type mentioned at the outset, which provides a high and adjustable sensitivity, a high readout speed, low costs per measuring point, and a large measuring range, and is suitable for integration into micro titer plates.

This task is performed by a sensor, associated illumination optics and a method to read out the sensor using the properties of the corresponding, independent patent claims.

The integrated-optical sensor includes an optical waveguide (2) with at least two incoupling regions (3, 5) for exciting guided waves, so-called modes. The coupling regions (3, 5) can be formed, for example, as grating couplers, or as prism couplers. Between the coupling regions (3, 5) the actual sensing area (4) is located, which is in contact with an analyte (8), and which comprises, in a preferred embodiment, an additional (bio-) chemical layer (7) for binding the molecules to be measured. The analyte (8) is in general a liquid or a gas in which these molecules are to be detected or in which the substances to be characterized are diluted. The presence of the molecules entails a change of the local index of refraction, influencing the propagation constant, or the effective index of refraction, of the waveguide (2). This requires that the bound molecules, and therefore the local index of refraction changes, are located within the evanescent field of the modes. A sensing wave (14) is stimulated in the waveguide (2) by an external sensing beam (12) through the first incoupling region (3), and which passes through the sensing area (4), is therefore experiencing a relative phase shift compared to the original state without the presence of the molecules to be measured. Now this phase shift is converted by a reference wave (15) into an intensity modulation, which can be measured by a suitable light detector (22). The reference wave (15) is excited in the second incoupling region (5), which is also passed through by the sensing wave (14). An interference of both waves after the second incoupling region (5) is not possible on its own, since by reciprocity of the coupling process, an incoupling region with which a waveguide mode is excited with good efficiency necessarily also couples out the biggest part of a waveguide mode incident in the incoupling region. According to the invention, the second incoupling region (5) is designed in a way that at least five percent, preferably a tenth or a fifth or one third, of the amplitude of the sensing wave (14) is preserved while traversing the second incoupling region (5) in order to achieve a measurable interference signal.

In a preferred embodiment of the invention, the second incoupling region (5) would be formed as a periodic grating coupler. The amplitude A of a waveguide mode passing through a periodical grating coupler is known to decrease exponentially according to $$A(z) = A_0 e^{\alpha z} \quad (1)$$

Where $A_0$ is the mode amplitude in front of the coupler, $\alpha$ the leakage factor and z the distance covered within the grating. The leakage factor can be tuned in a known manner, for example, by the form of the grating lines, the difference in refractive index at the grating lines, or the grating depth. According to the invention, the product of grating length $L_g$ and leakage factor $\alpha$ is limited by:

$$L_g \cdot \alpha \leq -\ln(0.05) \approx 3 \quad (2)$$

The formula is also valid for the case of a prism coupler, where the leakage factor can be adjusted by the distance to the waveguide (2). For an example grating length of $L_g = 200$ μm, the grating leakage factor may therefore not exceed 15 mm$^{-1}$. As mentioned, this corresponds to an especially "inefficient" coupler geometry. A low leakage factor can be achieved with a sine-shaped grating having a grating depth of about 5 . . . 15 nm in conventional waveguide geometries employed in (bio-) chemical sensors, consisting of a layer of 120 nm-150 nm thickness of a highly refractive metal oxide (n=2.1 . . . 2.4), based on the assumption of a measurement using TM modes.

The interference signal I within the waveguide (2) and after the second incoupling region (5) is calculated using $$I = A_m^2 + A_r^2 + 2 \cdot (A_m A_r) \cdot \cos(\phi_r - \phi_m) \quad (3)$$

Where $A_r$ and $\phi_r$ are the amplitude and phase of the reference wave (15), $A_m$ und $\phi_m$ are the amplitude and phase of the sensing wave (14), respectively, each behind the second incoupling region (5). According to the invention, the phase $\phi_m$ of the sensing wave (14) experiences the mentioned phase shift within the sensing area (4), so that the interference signal I varies sinusoidally according to the phase shift.

The arrangement according to the invention means that in comparison to existing sensors based on waveguides and grating or prism couplers, the sensing area (4) is thus separated from the incoupling region. The sensing method is not based on the readout of a wave guide coupler resonance, but on interferometry. This has the advantage that the sensing area is not limited by the scanning range of a parameter such as angle or wavelength, but rather by the coherence length of the light source (21). In another preferred embodiment, the sensor is also more robust with respect to manufacturing tolerances, as the modes can be excited in the waveguide (2) within a large angular range. This can be achieved in another preferred embodiment with short grating having a length of less than 400 μm and using focused light beams. Another advantage lies in the fact that the sensor is not susceptible to inhomogeneities within the sensing area (4).

In comparison to existing integrated-optical interferometric sensing methods, for example, Mach-Zehnder interferometers or such based on waveguides having several layers, the arrangement in the invention can be realized in a much more cost effective way, because the sensor platform consists only of one single planar waveguide (2) and several coupling regions.

In a further preferred embodiment of the invention, the sensor is suitable for the parallel readout of several signals, which up to now was only partly possible using interferometric sensors. To achieve this, the sensor has at least 3 or at least 7 sensing areas between the first and second incoupling regions (3, 5), which can be provided independently of each other with different adlayers (7), thus allowing the simultaneous detection of different substances. The first and second incoupling regions (3, 5) can have separate coupling pads per sensing area, in such a way that waves associated with the respective sensing areas are separated from each other in the waveguide (2) plane and in the direction perpendicular to mode propagation. In a cost effective embodiment, the sensor comprises one single coupling pad per incoupling region (3, 5), so that thereby, in principle, one single wave is excited, which undergoes a phase shift depending on the respective sensing area, and thus also depending on the position in the plane of the waveguide (2) and perpendicular to mode propagation. In a further embodiment, the sensor comprises one single detector measuring several interference signals, for example, using a line detector or a camera where several pixels are combined using an average value. In another exemplary embodiment, the sensor comprises one single detector per measurement channel corresponding to one single interference signal of a sensing area.

In another preferred embodiment of the invention, an outcoupling region (6) deflects the interference signal away from the waveguide (2) towards a detector or several detectors, such that several sensors can be placed one after the other on the same waveguide (2). As a result of this, the sensor becomes also suitable for a massive-parallel readout, and can be integrated, for example, into micro titer plates. The outcoupling region (6) can again comprise several outcoupling pads, each associated to a sensing area, or one single outcoupling pad which couples out all signals.

In a further preferred embodiment, a reference sensing area is associated to one or several sensing areas. This enables even the distinction of small signals from background variations caused by, for example, temperature or index of refraction variations in the analyte (8). Hence, to distinguish the useful signal from the background variations, all phases of the interference signals associated to the sensing areas (measuring channel) and the reference-sensing areas (reference channel) are determined. Then, the phases of the measuring channels are subtracted from the phases of the nearest reference channels, and the resulting differences are in general stored and displayed as a measurement value or measuring point.

The phase shift $\Delta \phi$ experienced by the sensing wave (14) while traversing the sensing area (4) is calculated by $$\Delta \phi = 2\pi / \lambda \cdot \Delta N \cdot L_m, \quad (4)$$

where $\lambda$ is the vacuum wavelength, $\Delta N$ is the induced change in effective refractive index, and $L_m$ is the length of the sensing area (4). Another advantage compared to existing sensors based on grating couplers is that the sensitivity of the sensor can be adjusted by the length of the sensing area (4). In another preferred embodiment, the length of the sensing area (4) is at least 1000 times the vacuum wavelength of the sensing wave (14) in order to achieve a high sensitivity.

The effective refractive index change $\Delta N$ can be itself estimated from the sensitivity S of the effective refractive index to the change of the measured parameter; for example, the increase in surface measured coverage $\Delta \Gamma$ of a (bio-) chemical substance:

$$\Delta N = \Delta \Gamma \cdot S \quad (5)$$

The order of magnitude of the sensitivity S is about $10^{-6}$ (pg/mm$^2$)$^{-1}$ for current waveguide geometries used in (bio-) chemical sensors and consisting of a layer of 120 nm-150 nm thickness of a highly refractive metal oxide (n=2.1 . . . 2.4), based on the assumption of a measurement using TM modes.

In an exemplary embodiment in which the adlayer (7) covers a 2-mm-long sensing area (4), and the sensor is read out at a wavelength of 650 nm, an increase of the antibody layer of 1 pg/mm$^2$ induces a phase shift of slightly more than 1° based on above statements.

In a further preferred embodiment of the invention, in order to measure such small changes of the interference signal phase shifts, the sensor comprises a phase modulator (24) with which the phase of either the sensing beam (12) or the reference beam (13) is scanned before impinging on the associated incoupling region (3, 5). Thereby, the associated wave in the waveguide (2) is also modulated in phase. Therefore the interference signal can be scanned over the whole phase range of the cosine-terms from equation (3), which allows in a known manner the exact determination of the phase shifts caused by the sensing area (4).

The advantage of modulating the interference signal in time, compared to the analysis of interferometry patterns as, for example, an image of interference fringes from a camera, consists in the fact that the determination of the phase is much less calculation-intensive and thus also less expensive. In addition, the readout is made easier, since a less exact positioning is necessary to record the useful signal.

In a further preferred embodiment of the invention, the phase modulator (24) is formed as a liquid crystal element. Thus the advantage of an external phase modulator (24) compared to integrated waveguide modulators becomes obvious, since modulators on the basis of a liquid crystal element can be cost-effectively mass produced. To manipulate the phase of the reference or the sensing wave (15, 14), a phase delay is introduced for the useful polarization pu of the reference or sensing beam (13, 12), which is coupled into the waveguide (2) through the associated incoupler. Thereto, the liquid crystal element is in general formed in a way so that the extraordinary axis of the liquid crystal, which can be adjusted by a voltage, lies in the same plane as the useful polarization pu.

In a further preferred embodiment of the invention, the liquid crystal in the liquid crystal element has no twist or a twist of no more than 20°, and at least one substrate (31) or (32) of the liquid crystal element is equipped with a rubbing direction (r1, r2), or planar orientation of the surface liquid crystal molecules, which lies in the same plane as the useful polarization pu. In doing so, the extraordinary axis of the liquid crystal, which can be adjusted by a voltage, lies in the same plane as the useful polarization pu.

In a further preferred embodiment of the invention, a polarizer is attached at least behind the second substrate (32) which is oriented towards the incoupling region (3, 5), namely only in a region illuminated by a phase reference beam (17). If the phase reference beam (17) is not already polarized in a suitable manner, a first polarizer (33) can be attached in front of the first substrate (31). An absolute phase shift produced by the liquid crystal element can thereby be determined using an additional phase-reference detector. As a result of this, the absolute value of the scanned parameter is measurable, which was not possible in existing measuring methods. Therefore a higher accuracy can be reached, since variations of the scanned parameter can be compensated, for instance by subtracting the phase determined for each channel from the phase of the phase modulator.

In a further preferred embodiment of the invention, the liquid crystal element has split electrodes to form two separately controllable regions. The advantage of this is that a further degree of freedom is provided for controlling the phase, so that, for example, the phase of the sensing beam (12) and the phase of the reference beam (13) can be modulated alternatively. Another advantage consists in the fact that the reference beam (13) and the sensing beam (12) can be placed much closer together, since the edge region of the liquid crystal element does not lie between them.

In a further preferred embodiment, the phase shift induced by the sensing fields is determined using a quadrature measurement. Hereto, two interference signals which are phase-shifted by 90° are recorded per sensing field, so that the absolute phase shift induced by the sensing field can be determined in known manner.

In another preferred embodiment, two coupling pads are associated to every sensing field in the first or second incoupling region (5), distinguished by a different substrate thickness, so that the mentioned phase shift of around 90° occurs. The difference of the substrate thickness $\Delta h_s$ should therefore be around $$\Delta h_s = \lambda \cdot \cos(\theta)/(4 \cdot (n_s - n_a))$$

Where θ is the average angle of incidence of the associated ray, $n_s$ the index of refraction of the substrate (1), and $n_a$ the index of refraction of the environment, in general air with $n_a=1$.

In a further preferred embodiment of the invention, the adlayer (7) is shorter than the sensing area (4) by at least one third. Thereby a specific reduction of the sensitivity is achieved. This is an advantage, for example, when different substances of much different concentrations are measured, or if different sensitivities should be used for verifying measured data. While this is not possible as such for existing methods based on grating couplers or prism couplers, it is achieved for a sensor according to the invention by a simple reduction of the adlayer (7) length.

In a further preferred embodiment the first and the second incoupling regions (3,5) are not in contact with the analyte (8). The advantage of this is that the excitation of the waves in the waveguide (2) is not influenced by the index of refraction of the analyte (8).

In a further preferred embodiment, the sensor comprises a cover (40) containing the grating structures. Brought into sufficiently close contact with the waveguide (2), the grating structures can be used for exciting waves in the waveguide (2). This has the advantage of a separation of the manufacture of the waveguide (2) and the grating, and therefore, for example, the waveguide (2) can be produced on a high quality glass substrate (1), while the grating can be manufactured by a mass production method in a plastic cover (40), such as for example using molding, casting, or hot embossing.

In further preferred embodiments, possible parasitic reflections are avoided, the latter being caused by the border between the cover (40) and the analyte (8). This is achieved by an oblique incidence of the waves on the borders, such that the reflections are not able to interfere with each other. This is preferably achieved by forming the borders in a diagonal manner, by placing the grating couplers diagonally, or by an oblique incidence of the beams.

Preferred illumination optics (23) for the sensor do not make use of beam splitters, but use different angular regions of the emission of a laser diode to generate sensing beam (12), reference beam (13), and optionally a phase reference beam (17). This is known from other interferometric measurement units, as for example Rayleigh interferometers.

In another preferred embodiment of the illumination optics (23) for a sensor, according to the invention, an optical element (56) is introduced, which deflects one of either the sensing beam or reference beam (12, 13) by a certain angle γ of greater than 1° and smaller than 45° compared to the other beam. After that, both beams are focused by a cylindrical lens onto the corresponding coupling pads. The relation between the angle γ, the distance w of the cylindrical lens to the deflection element (56), and the distance d between the centers of both angular regions on the deflection element (56), and the distance p between the first incoupling region (3) and the second incoupling region (5) is preferably at least close to:

$$d+p=\sin(\gamma)*w$$

In addition, the focal length fl of the cylindrical lens is preferably at least close to:

$$fl=p/\sin(\gamma)$$

Using this choice of the distances between the elements, as well as the focal length of the cylindrical lens, it is achieved that sensing beam and reference beam (12, 13) are incident on the sensor at a distance p, and show a similar angle spectrum.

BRIEF DESCRIPTION OF THE DRAWINGS

In the following, the object of the invention is explained in more detail on the basis of preferred examples of embodiments, which are illustrated in the annexed drawings. They respectively schematically depict.

DETAILED DESCRIPTION OF THE INVENTION

Figure 1:
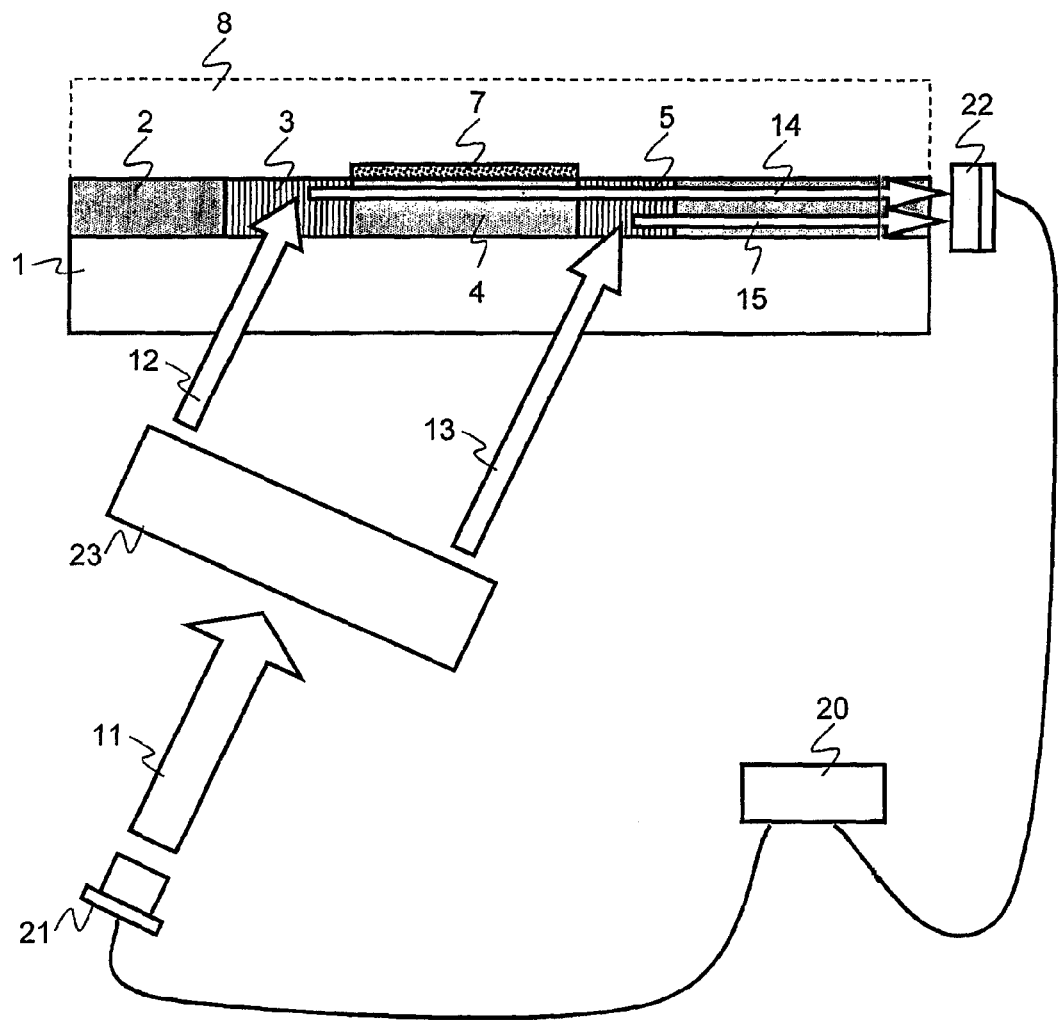
FIG. 1-4 Cross sections of sensors and corresponding light paths

FIG. 1 illustrates a cross section of a sensor and corresponding light paths. The sensor comprises a light source (21), which irradiates illumination optics (23). The light source (21) is preferably a diode laser with a wavelength from 400 nm to 800 nm, but preferably with a wavelength of 635 or 650 nm. The illumination optics (23) divide the beam into two parts, namely a sensing beam (12) and a reference beam (13) which are incident on incoupling regions (3, 5) of the waveguide (2) preferably through a substrate (1). The sensing beam (12) excites a sensing wave (14) in a waveguide (2) through a first incoupling region (3), the former subsequently traversing a sensing area (4). The sensing area (4) is provided with an additional layer (7) which can bind a (bio-) chemical substance from the analyte (8). The analyte (8) can be either a liquid or a gas. Through the second incoupling region (5) a reference wave (15) is excited in the waveguide (2) by the reference beam (13). The sensing wave (14) passes through the second incoupling region (5) and is thereby attenuated. According to the invention the sensing wave (14) is attenuated by the second incoupling region (5) at most to five percent of its amplitude in front of the second incoupling region (5), and preferably at most to a tenth or to one fifth or to one third. Behind the second incoupling region (5), both waves, (14) and (15), interfere, so that the interference signal can be recorded by a suitable detector (22), preferably by a photodiode, a CMOS camera or a line detector. The light source (21) and the detector (22) are preferably controlled, or read out, by the same control unit (20). In a preferred embodiment the waveguide (2) consists of a layer of 120 nm-150 nm thickness made from highly refractive metal oxide (n= 2.1 . . . 2.4), and is excited by TM polarization, and the incoupling regions (3, 5) comprise gratings of a length of 200 μm, which are etched into the waveguide (2) or in the substrate (1) under the waveguide (2) in a known manner to a depth of about 5 . . . 15 nm.

Figure 2:
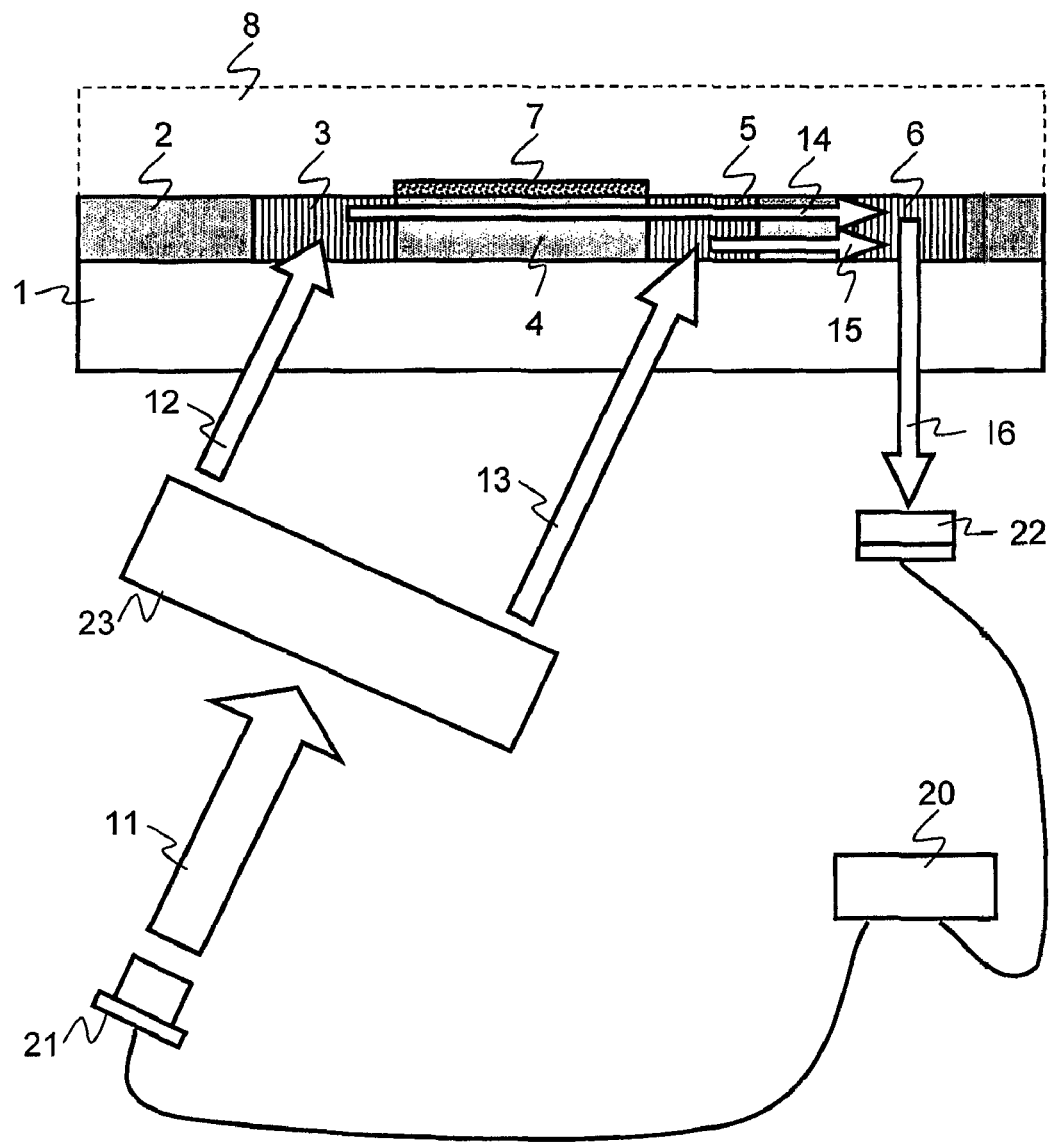

FIG. 2 illustrates another cross section through a sensor and corresponding light paths. Behind the second incoupling region (5) an outcoupling region (6) is provided by which the interference signal is coupled out and impinges on the detector (22) as signal beam (16). In a preferred embodiment, the outcoupling region (6) comprises grating couplers, which have a different grating period than the incoupling gratings.

Figure 3:
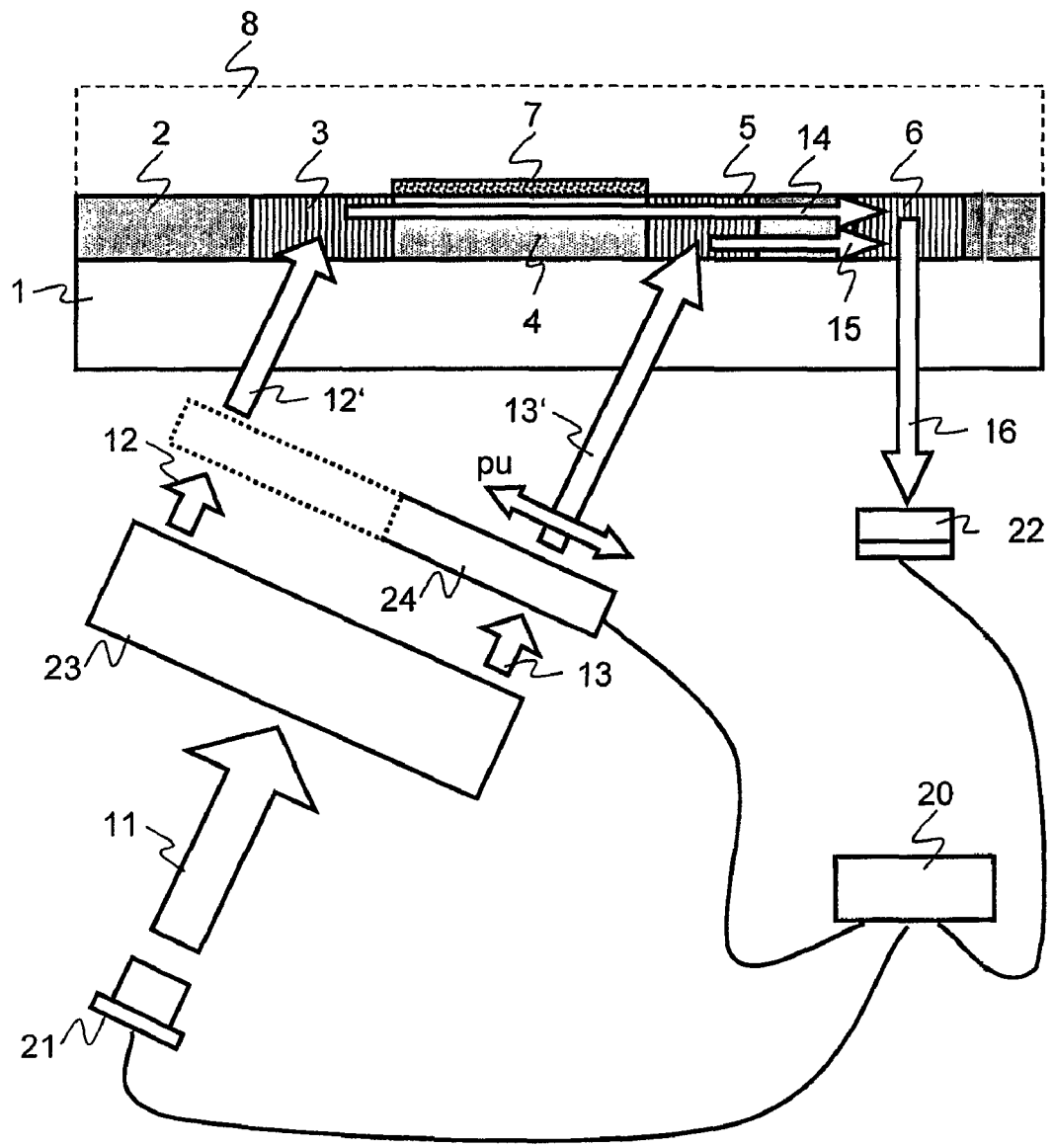

FIG. 3 illustrates another cross section through a sensor and corresponding light paths. A phase modulator is provided in the path of the reference beam (13), such as the phase of the reference beam (13) (13') can be modulated after emerging from the phase modulator according to the setting of a control unit (20). To achieve this, the useful polarization direction pu, at least, is phase-modulated. The direction of the useful polarization pu depends on the polarization of the waves to be excited in the waveguide (2). The illustrated preferred polarization direction perpendicular to the propagation of the light beam and in the plane of the page is suitable to stimulate TM waves in the waveguide (2). In the case of the excitation of TE waves (not depicted), the useful polarization direction pu lies perpendicular to the propagation of the light beam and perpendicular to the plane of the page. Preferably, the sensing beam (12) can be also phase-modulated in, so that the phase of the sensing beam (12') can be modulated after emerging from the phase modulator according to the setting of a control unit (20). Thereby, an interference signal based on the setting of the control unit is created, which is recorded by the detector (22), and is evaluated by the control unit (20).

Figure 4:
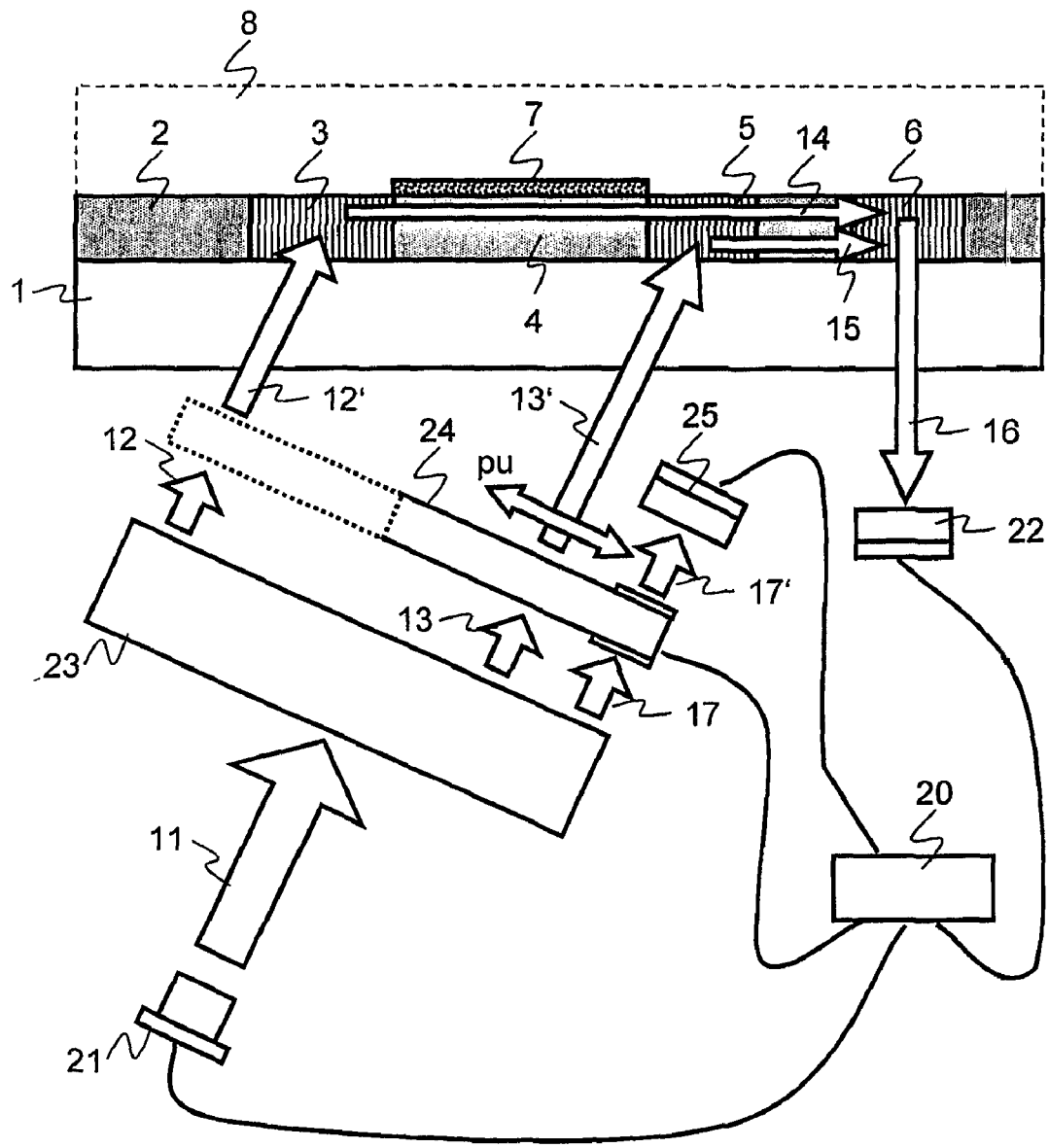

FIG. 4 illustrates another cross section of a sensor and corresponding light paths. In addition, two polarizers (33, 34) are attached, which are passed through by a phase reference beam (17). The phase reference beam (17) can be modulated in intensity through the suitable orientation of the polarizers (33, 34), displayed in FIG. 7. Afterwards, this intensity modulation is recorded by a phase reference detector (25), and is evaluated by the control unit (20).

Figure 5:
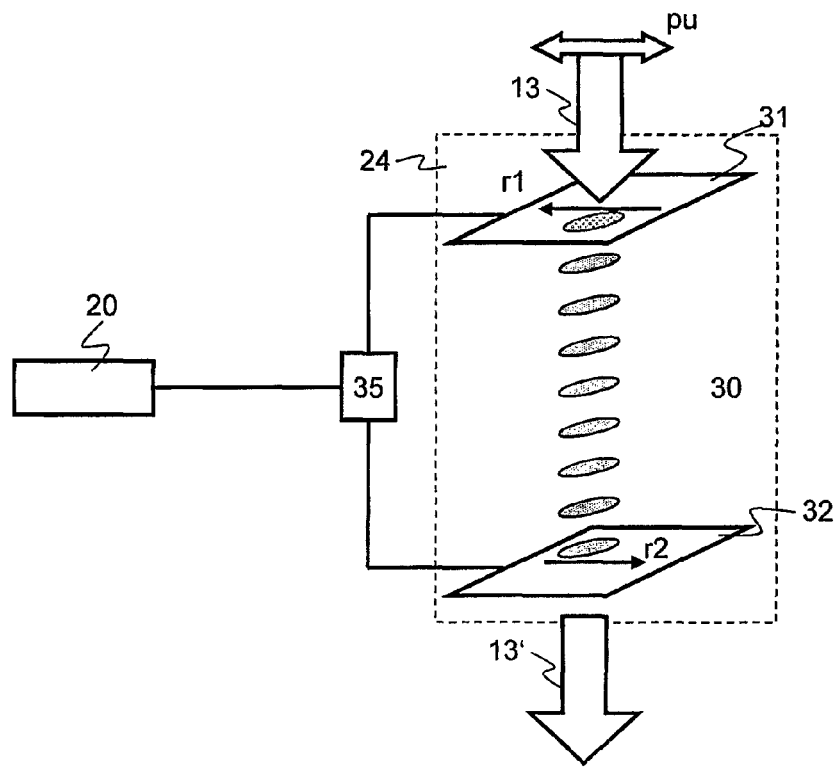
FIG. 5-7 Layer successions of liquid crystal cell phase modulators

FIG. 5 illustrates a layer succession of a liquid crystal cell phase modulator (24). The liquid crystal cell consists of a first and second substrate with electrodes (31, 32), and a nematic liquid crystal layer sandwiched in between (30). The molecules in the boundary regions of the substrates (31, 32) are oriented in a known manner, preferably by a rubbed polyimide layer, in a direction anti-parallel to the directions r1 and r2, so that the extraordinary axis of the liquid crystal molecules lies in the plane of the direction of the useful polarization pu. In addition, the liquid crystal between the substrates (31, 32) has no, or only a small, twist. The alignment of the liquid crystal molecules can be modified in a known manner by applying a voltage through the voltage source (35) and set by the control module, so that the phase of the light beam is modulated accordingly in the useful polarization direction pu. In a preferred embodiment the cell has a gap of 4 μm filled with a liquid crystal having a birefringence of Δn≈0.23 (as for example liquid crystals with product name Merck E7).

Figure 6:
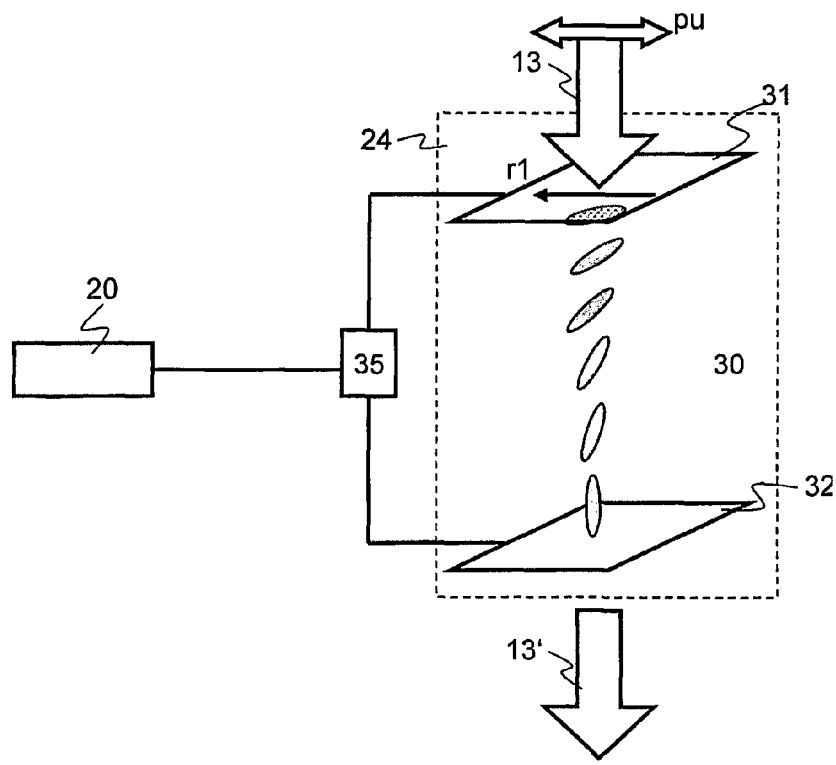

FIG. 6 illustrates another layer succession of a liquid crystal cell phase modulator (24). Here, only the first substrate (31) includes a planar orientation layer in the direction r1 of the useful polarization pu, while the second one (32) includes a homeotropic orientation layer. The resulting so-called Hybrid Aligned Nematic (HAN) cell has the advantage of shorter molecule reorienting times, called switching times. In another preferred embodiment (not illustrated), the first substrate layer (31) comprises a homeotropic orientation layer, and the second substrate layer (32) comprises a planar orientation layer in the direction of the useful polarization pu. In a preferred embodiment the cell has a gap of 6 μm filled with a liquid crystal having a birefringence of Δn≈0.23 (as for example liquid crystals with product name Merck E7).

Figure 7:
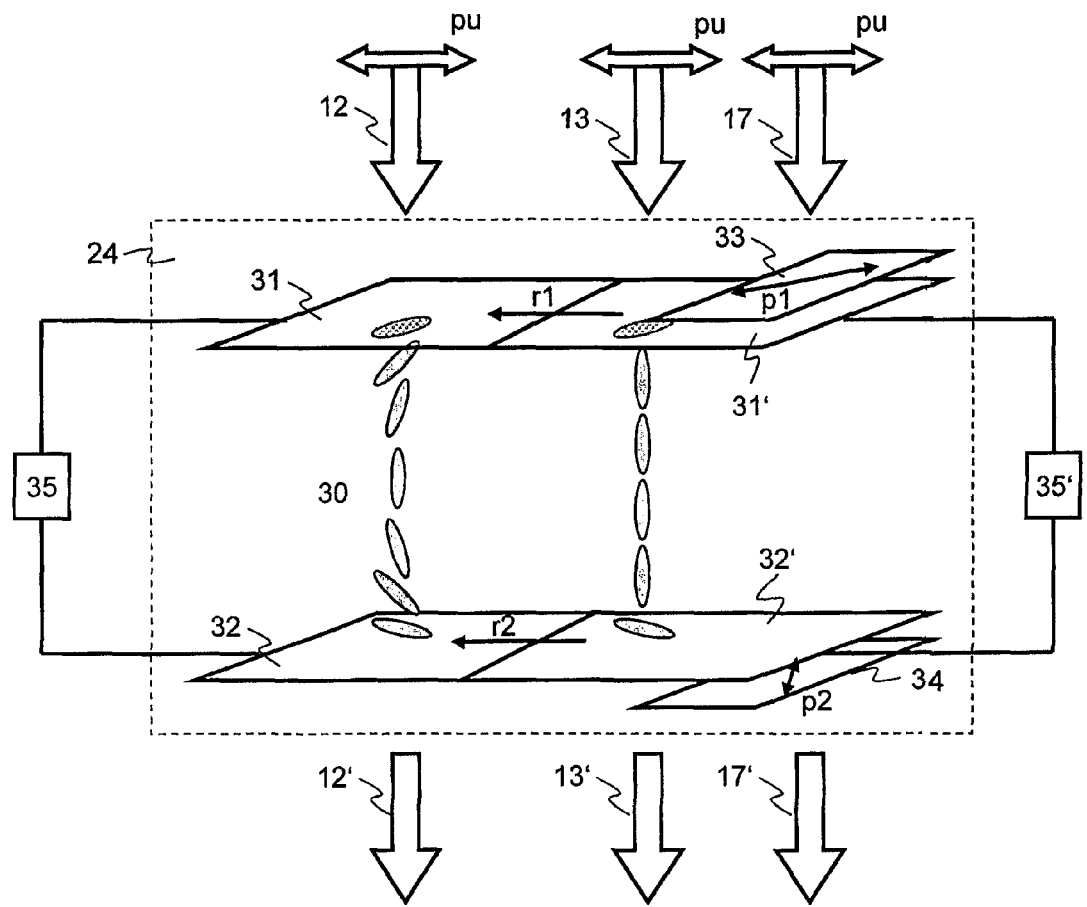

FIG. 7 illustrates another layer succession of a liquid crystal cell phase modulator (24). In this further preferred embodiment, both electrodes on the substrates are divided into two partial electrodes (31, 31') and (32, 32'), so that two different areas are created within the liquid crystal cell, which can be independently controlled by two voltage sources (35', 35") depending on the setting of a control unit (not illustrated). The area illuminated by the reference beam (13) is illustrated in the activated state (that is, a voltage is applied), while the area illuminated by the sensing beam (12) is illustrated in the inactivated state (that is, no voltage is applied). In the illustrated preferred embodiment, the liquid crystal element is a so-called Pi cell and both substrates (31.31'), (32.32') comprise a planar rubbed orientation layer in the directions r1, r2 being mutually parallel. This cell has the advantage of even faster switching times than the HAN cell. In a preferred embodiment, the cell has a gap of 6 μm filled with a liquid crystal having a birefringence of Δn≈0.23 (as for example liquid crystals with product name Merck E7).

In a further preferred embodiment (not illustrated), only one partial area defined by the electrode separation is controlled, while the electrodes of the second partial area are short-circuited. In another embodiment (not illustrated), only one of both electrodes (31, 32) is divided, while the other spans both partial areas.

In a further preferred embodiment, polarizers (33, 34) are additionally attached to both substrates (31, 32), which in known manner convert the phase modulation of a phase reference beam (17) into an intensity-modulated beam (17'). To achieve this, the polarizers (33, 34) are attached to form an angle preferably at least close to 45° with respect to the rubbing directions r1, r2.

Figure 8:
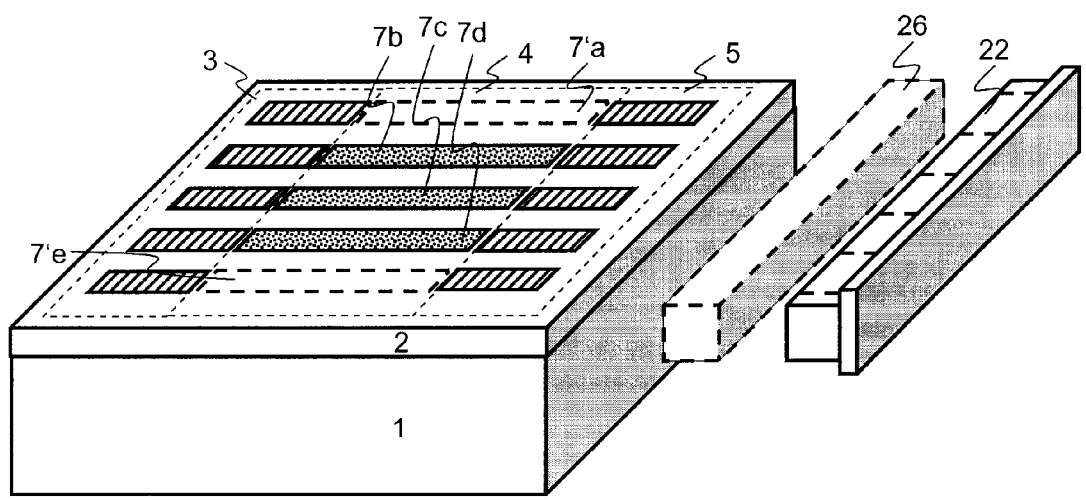
FIG. 8-9 Perspective view of sensors

FIG. 8 illustrates the perspective view of a sensor comprising five sensing channels. The sensor comprises three different adlayers (7b, 7c, 7d) within the sensing area (4), which can bind different substances from the analyte (8) (not displayed, in contact with the adlayers). In addition, the sensor comprises two reference sensing fields (7'a, 7'e) without additional layers, delivering a background signal. The sensor preferably comprises optional imaging optics (26) with which the interference signals at the waveguide face (not displayed) are focused onto the detector (22). The imaging optics (26) consist preferably of a positive cylinder lens, and the detector (22) consists preferably of a line camera. In another preferred embodiment, a discrete detector, preferably a photodiode, is associated to every sensing channel.

Figure 9:
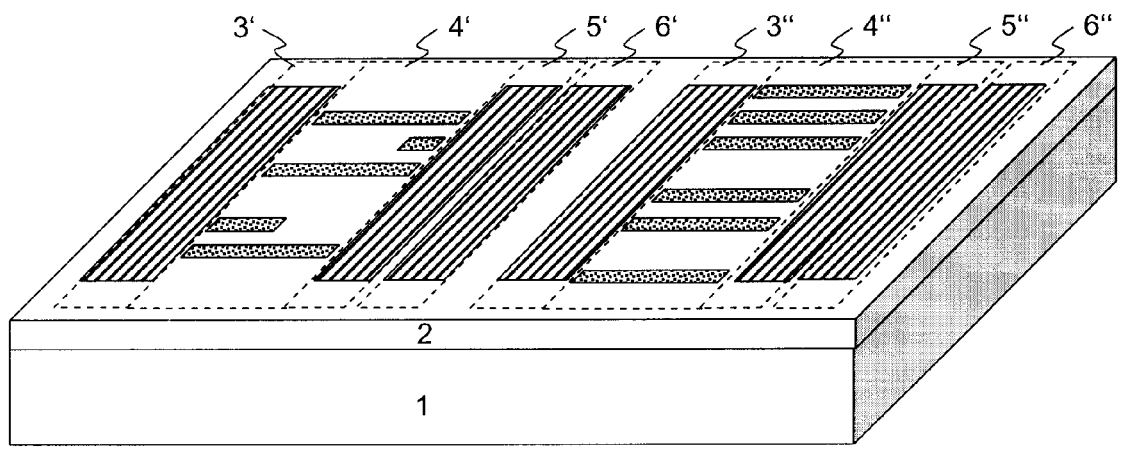

FIG. 9 illustrates the perspective view of a sensor comprising 16 sensing channels. As in the previous embodiment, the sensor comprises two first incoupling regions (3', 3"), two sensing areas (4', 4"), two second incoupling regions (5', 5") and two outcoupling regions (6', 6"). The incoupling regions (3', 3", 5', 5") and outcoupling regions (6', 6") comprise one single continuous coupling pad.

Figure 10:
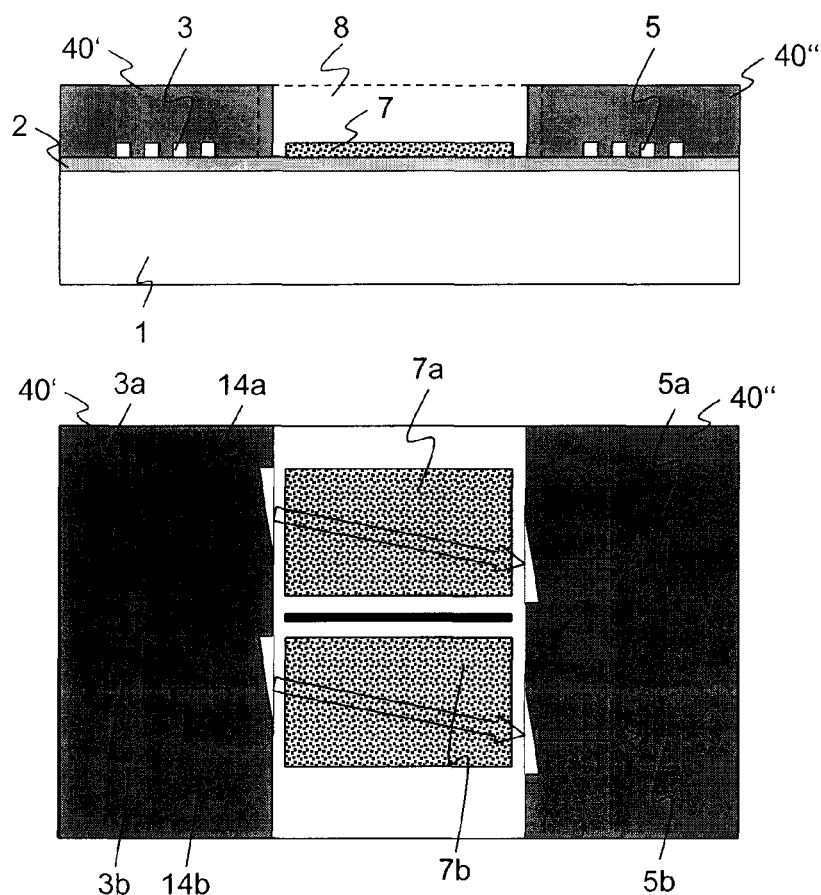
FIG. 10-12 Cross section and top view of a sensor

FIG. 10 illustrates the cross section and top view of a sensor, where the coupling regions are formed as gratings in a cover (40', 40") being in contact with the waveguide (2). Thereby, the coupling gratings are not in contact with the analyte (8), and can be manufactured at a reasonable price. To avoid the influence of parasitic reflections (not displayed), which are caused by the border between the cover (40', 40") and the analyte (8) due to the difference in index of refraction, the separating wall is placed askew, with respect to the grating lines, by between 5° and 45°, according to the invention. In a preferred embodiment, the cover (40', 40") consists of a replicated part made of PMMA, and the grating formed out in it is placed closer than 50 nm to the waveguide (2).

Figure 11:
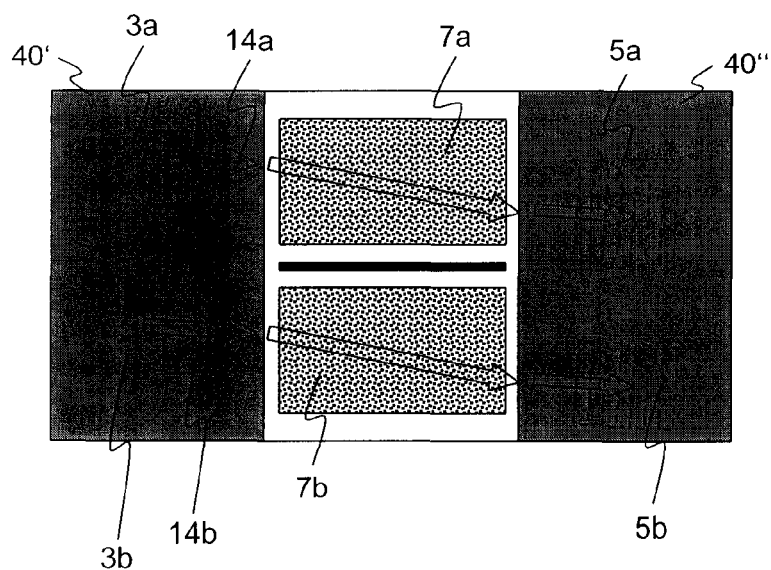

FIG. 11 illustrates the top view of a sensor, wherein the coupling regions are formed as a grating in a cover (40', 40") being in contact with the waveguide (2). In doing so, the grating is placed askew, with respect to the grating lines, by between 5° and 45°, according to the invention, to avoid the influence of parasitic reflections (not displayed).

Figure 12:
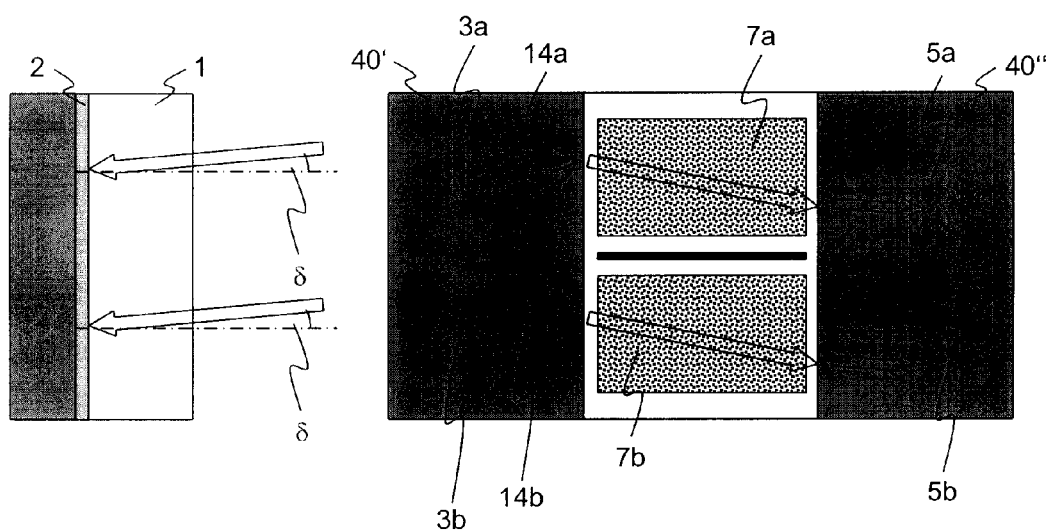

FIG. 12 illustrates the top view of a sensor, wherein the first and second incoupling gratings are illuminated under an oblique angle δ of over 5°, so that the sensing waves (14) and reference waves (14) propagate in a direction not perpendicular to the grating lines and the border of the described plastic cover (40', 40") to avoid the influence of parasitic reflections (not displayed).

Figure 13:
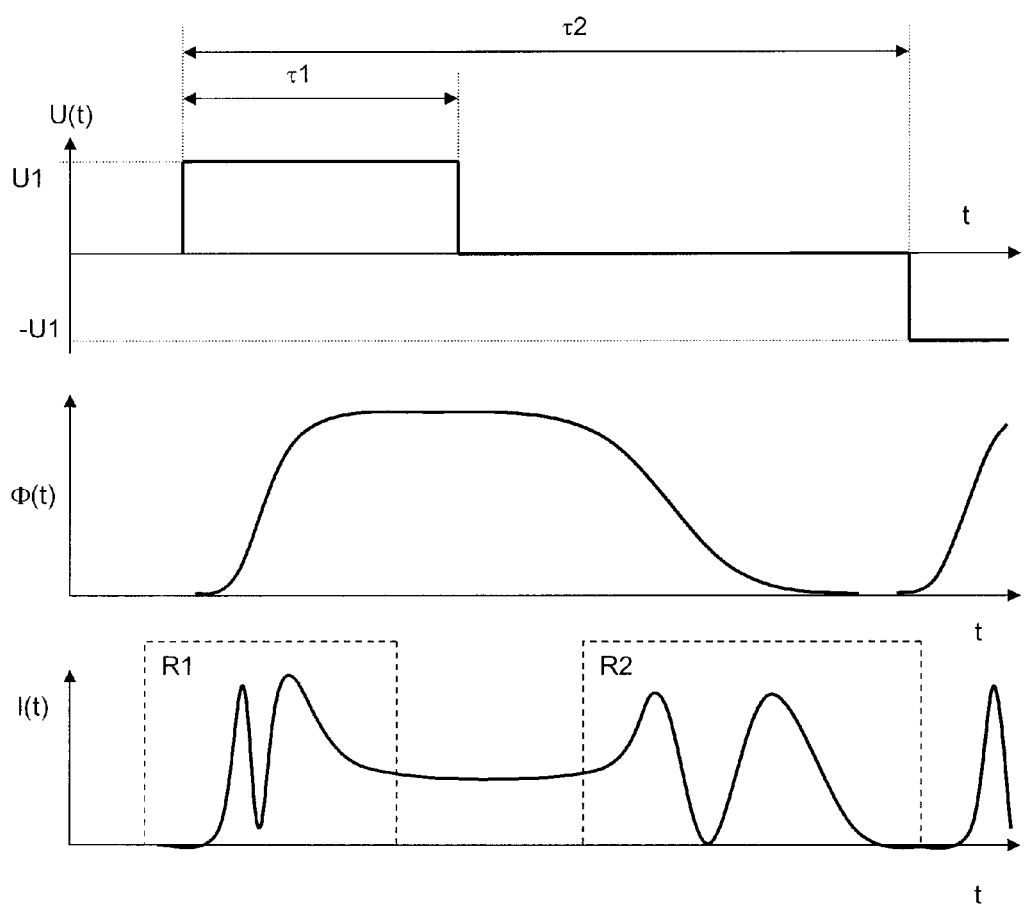
FIG. 13 Signal trajectory of a phase modulator control, and corresponding phases and interferogram trajectory The reference marks utilized in the drawings and their significance are listed in summary in the list of reference marks. Principally in the figures the same parts are identified with the same reference marks.

FIG. 13 illustrates a signal trajectory of a phase modulator control, and corresponding phases and interferogram trajectory. The upper graph shows a periodic square signal with amplitude U1, period τ2 and duration τ1 which is used to control the modulator, especially to control a liquid crystal cell. The middle graph shows the trajectory of the phase depending on the voltage regulation. In the case of a liquid crystal modulator, the inertia of the molecules causes a delay for the modulator to reach the maximum phase modulation with respect to the voltage regulation, typically some hundred microseconds or some milliseconds. When switching off the voltage, this phenomenon is even more marked; that is, the molecules return to their original position only after a longer time of typically some milliseconds. The lower graph shows the trajectory of an intensity modulation, for example the interference signal between the sensing wave (14) and the reference wave (15), or the phase reference signal modulated in intensity. Two measuring regions R1 and R2 can be identified, in which the corresponding interference signal can be recorded.

In a preferred embodiment, a liquid crystal modulator is operated using a square wave voltage having an amplitude of U1=5V, a frequency 1/τ2 of 50 Hz and a sampling rate τ1/τ2 of 0.2.

List of Reference Marks
1 Substrate
2 Waveguide
3 First incoupling region
4 Sensing area
5 Second incoupling region
6 Outcoupling region
7 Adlayer
8 Analyte
11 Light beam
12 Sensing beam
13 Reference beam
14 Sensing wave
15 Reference wave
16 Signal beam
17 Phase reference beam
20 Control unit
21 Light source
22 Detector
23 Illumination optics
24 Phase modulator
25 Phase reference detector
26 Imaging optics 30 Liquid crystal layer
31 First substrate with electrode
32 Second substrate with electrode
33 First polarizer
34 Second polarizer
35 Voltage source
40 Cover
51 Collimation optics
52 Focusing optics
53 Beam splitter
54 Deflection mirror
55 Diaphragm
56 Optical deflection element

The invention claimed is:

1. Integrated-optical sensor, comprising
   An optical waveguide (2) having at least a first incoupling region (3), wherein a sensing wave (14) is excited by a sensing beam (12), and a second incoupling region (5), wherein a reference wave (15) is excited by a reference beam (13), and an interference signal is created between the sensing wave (14) and the reference wave (15),
   at least one sensing area (4) located between, and in a direction of the waveguide's mode propagation in line with, the first (3) and the second (5) incoupling regions and passed through by the sensing wave (14), wherein a change of the propagation constant of the waveguide (2), and thus a phase shift of the sensing wave (14), occurs depending on the optical environment,
   at least one detector (22) for measuring of an interference signal between the sensing wave (14) and the reference wave (15),
      wherein at least a part of the sensing wave (14) passes through the second incoupling region (5) after the sensing area (4), and the second incoupling region is constructed such that the ratio of the amplitudes of the sensing wave (14) in front and behind the second incoupling region (5) is 20:1 at most, and
      wherein the interference signal is guided within the optical waveguide (2), and
      wherein the optical waveguide is a light conduit of solid dielectric material adjacent to another solid dielectric material of lower refractive index.

2. Integrated-optical sensor according to claim 1, wherein the ratio of the amplitudes of the sensing wave (14) in front and behind the second incoupling region (5) is at most 10:1.

3. Integrated-optical sensor according to claim 1, wherein the sensing area (4) has a length of at least 1000 times the vacuum wavelength of the sensing wave (14).

4. Integrated-optical sensor according to claim 1, wherein the sensing area (4) comprises at least one adlayer (7) which binds at least partially at least one substance to be measured and contained in an analyte (8) being in contact with the adlayer (7).

5. Integrated-optical sensor according to claim 4, further comprising at least one reference sensing area without an additional layer (7) between the first and second incoupling region (3, 5) for the determination of a background signal.

6. Integrated-optical sensor according to claim 4, comprising between the first and second incoupling region (3,5) at least three or at least seven sensing regions having different adlayers (7) for the parallel measurement of several substances.

7. Integrated-optical sensor according to claim 1, wherein all incoupling regions (3, 5) and outcoupling regions (6), combined designated as coupling regions (3, 5, 6), are formed as grating couplers.

8. Integrated-optical sensor according to claim 7, further comprising a coherent light source (21) and illumination optics (23), wherein the coupling regions (3, 5, 6) have a length of only 400 µm, and the light from the light source (21) is focused at least partially by the illumination optics (23) onto the incoupling regions (3, 5).

9. Integrated-optical sensor according to claim 7, wherein the coupling regions (3, 5, 6) comprising grating structures are not in contact with the analyte (8), and wherein the coupling regions (3, 5, 6) are formed as grating structures at the surface of a cover (4) being in contact with the waveguide (2).

10. Integrated-optical sensor according to claim 1, further comprising at least one phase modulator (24) for modifying the phase of at least one polarization direction of the sensing beam (12) and/or the reference beam (13).

11. Integrated-optical sensor, comprising:
    An optical waveguide (2) having at least a first incoupling region (3), wherein a sensing wave (14) is excited by a sensing beam (12), and a second incoupling region (5), wherein a reference wave (15) is excited by a reference beam (13),
    at least one sensing area (4) located between the first (3) and the second (5) incoupling regions and passed through by the sensing wave (14), wherein a change of the propagation constant of the waveguide (2), and thus a phase shift of the sensing wave (14), occurs depending on the optical environment,
    at least one detector (22) for measuring of an interference signal between the sensing wave (14) and the reference wave (15)
    further comprising at least one phase modulator (24) for modifying the phase of at least one polarization direction of the sensing beam (12) and/or the reference beam (13)
       wherein at least a part of the sensing wave (14) passes through the second incoupling region (5) after the sensing area (4), and the ratio of the amplitudes of the sensing wave (14) in front and behind the second incoupling region (5) is 20:1 at most, and
       wherein the phase modulator (24) is formed as a liquid crystal element, which is controllable by an applied voltage, and comprising a first substrate with electrode (31), a second substrate with electrode (32), and a liquid crystal layer (30) in between.

12. Integrated-optical sensor according to claim 11, wherein the liquid crystal element comprises a nematic liquid crystal comprising no twist or a twist of less than 20°, and wherein at least one substrate (31) or (32) of the liquid crystal element causes a planar direction (r1, r2) of orientation of the boundary liquid crystal molecules, thus defining the extraordinary axis of the liquid crystal element which is at least close to parallel to the associated light beam's polarization direction (pu) corresponding to the polarization of the wave excited in the waveguide (2).

13. Integrated-optical sensor according to claim 12, wherein furthermore a polarizer (34) is attached at least to the second substrate (32) in a region illuminated by a phase reference beam (17) generated by the lighting optics (23), and wherein the phase reference beam (17) is modulated in the intensity by the polarizer (34), and a phase reference detector (25) measures the intensity of the modulated phase reference beam (17').

14. Integrated-optical sensor according to claim 13, wherein parasitic interferences originating from multiple reflections of sensing waves (14) are avoided, by placing the border edge of the cover (40), passed through by the sensing wave (14), askew at an angle between 5° and 45° with respect to the grating lines, or by illuminating the first and second incoupling regions (3,5) obliquely by the sensing beam (12) and reference ray (13) at an angle δ of greater than 5°, such as the sensing waves (14) and reference waves (15) propagate in a direction not perpendicular to the grating lines and the border edges of the cover (40).

15. Integrated-optical sensor according to claim 11, wherein at least one electrode (31,32) of the liquid crystal element comprises two independently controllable regions, wherein the first region (31,32) is illuminated by the sensing beam (12) and the second region (31', 32') is illuminated by the reference beam (13).

* * * * *